(12) United States Patent
Khamaysi et al.

(10) Patent No.: US 11,740,225 B2
(45) Date of Patent: Aug. 29, 2023

(54) CYST FLUID VISCOSITY AS A MARKER FOR MALIGNANCY

(71) Applicants: RAMBAM MED-TECH LTD., Haifa (IL); TECHNION RESEARCH & DEVELOPMENT FOUNDATION LTD., Haifa (IL)

(72) Inventors: Iyad Khamaysi, Kfar Kana (IL); Eyal Zussman, Haifa (IL)

(73) Assignees: TECHNION RESEARCH & DEVELOPMENT FOUNDATION LTD., Haifa (IL); RAMBAM MED-TECH LTD., Haifa (IL)

( * ) Notice: Subject to any disclaimer, the term of this patent is extended or adjusted under 35 U.S.C. 154(b) by 1515 days.

(21) Appl. No.: 15/972,671

(22) Filed: May 7, 2018

(65) Prior Publication Data

US 2018/0321217 A1 Nov. 8, 2018

Related U.S. Application Data

(60) Provisional application No. 62/502,693, filed on May 7, 2017.

(51) Int. Cl.
*G01N 33/487* (2006.01)
*G01N 33/574* (2006.01)
*A61B 10/04* (2006.01)
*A61B 17/34* (2006.01)
*G01N 11/14* (2006.01)

(52) U.S. Cl.
CPC .......... *G01N 33/487* (2013.01); *A61B 10/04* (2013.01); *A61B 17/3403* (2013.01); *G01N 33/57438* (2013.01); *A61B 2010/045* (2013.01); *A61B 2017/3413* (2013.01); *G01N 11/14* (2013.01); *G01N 2203/0089* (2013.01); *G01N 2333/705* (2013.01); *G01N 2333/928* (2013.01)

(58) Field of Classification Search
None
See application file for complete search history.

(56) References Cited

U.S. PATENT DOCUMENTS

| 4,173,142 A | * | 11/1979 | Heinz | ................. G01N 11/142 73/54.32 |
| 2002/0116987 A1 | * | 8/2002 | Braithwaite | ............ G01N 3/08 73/54.01 |

OTHER PUBLICATIONS

Lewandrowski KB, Southern JF, Pins MR, Compton CC, Warshaw AL. Cyst fluid analysis in the differential diagnosis of pancreatic cysts. A comparison of pseudocysts, serous cystadenomas, mucinous cystic neoplasms, and mucinous cystadenocarcinoma. Ann Surg. Jan. 1993;217(1):41-7. (Year: 1993).*

Al-Haddad M et al.: "Performance characteristics of molecular (DNA) analysis for the diagnosis of mucinous pancreatic cysts", Gastrointestinal endoscopy, Jan. 2014, pp. 79-87, vol. 79, No. 1.

(Continued)

*Primary Examiner* — Paul M. West
*Assistant Examiner* — Mark A Shabman
(74) *Attorney, Agent, or Firm* — The Roy Gross Law Firm, LLC; Roy Gross (57) ABSTRACT

The present invention provides methods for determining malignancy in a cyst by measuring viscosity of cyst fluid while under stain. The invention further provides devices, and computer program products for determining same.

19 Claims, 5 Drawing Sheets

(56) References Cited

OTHER PUBLICATIONS

DiMaio CJ et al.: "Pancreatic cyst fluid concentration of high-mobility group A2 protein acts as a differential biomarker of dysplasia in intraductal papillary mucinous neoplasm", Gastrointestinal endoscopy, Jun. 2016, pp. 1205-1209, vol. 83, No. 1.
Leung KK et al.: "Pancreatic cystic neoplasm: the role of cyst morphology, cyst fluid analysis, and expectant management", Annals of surgical oncology, Oct. 2009, pp. 2818-2824, vol. 16, No. 10.
Linder JD et al.: "Cyst fluid analysis obtained by EUS-guided FNA in the evaluation of discrete cystic neoplasms of the pancreas: a prospective single-center experience", Gastrointestinal endoscopy, Nov. 2006, pp. 697-702, vol. 64 No. 5.
Nagashio Y et al.: "Combination of cyst fluid CEA and CA 125 is an accurate diagnostic tool for differentiating mucinous cystic neoplasms from intraductal papillary mucinous neoplasms", Pancreatology : official journal of the International Association of Pancreatology, Nov.-Dec. 2014, pp. 503-509, vol. 14 No. 6.
Snozek CL et al.: "Use of cyst fluid CEA, CA19-9, and amylase for evaluation of pancreatic lesions", Clinical biochemistry, Oct. 2009, pp. 1585-1588, vol. 42, No. 15.
Suzuki R et al.: "Diagnostic yield of EUS-FNA-based cytology distinguishing malignant and benign IPMNs: a systematic review and meta-analysis", Pancreatology : official journal of the International Association of Pancreatology, Sep.-Oct. 2014, pp. 380-384, vol. 14, No. 5.

\* cited by examiner

Diagonal segments are produced by ties.

Figure 4B

|  | AUC (95% CI) | P value |
|---|---|---|
| Age (60 y) | 0.933 (0.829 – 1.00) | 0.001 |
| CEA (1000 ng/mL) | 0.767 (0.560 – 0.974) | 0.035 |
| Viscosity, $\eta_c$ | 0.817 (0.620 – 1.00) | 0.012 | ns
CYST FLUID VISCOSITY AS A MARKER FOR MALIGNANCY

RELATED APPLICATIONS

This application claims the benefit of priority of U.S. Provisional Application No. 62/502,693 filed on May 7, 2017 entitled "CYST FLUID VISCOSITY AS A MARKER FOR MALIGNANCY". The contents of the above application is incorporated by reference as if fully set forth herein in its entirety.

FIELD OF INVENTION

The present invention relates to methods for determining malignancy in a cyst based on viscosity of cyst fluid.

BACKGROUND OF THE INVENTION

Figure 1:
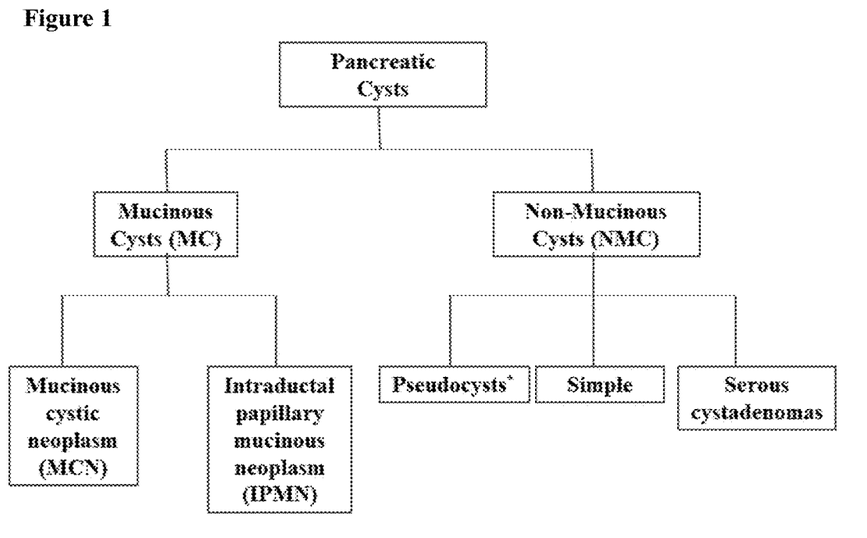
FIG. 1. Classification of pancreatic cysts.

Pancreatic cancer is the fourth leading cause of cancer deaths among men and women, accounting for 6% of all cancer-related deaths, with a collective median survival time of 4-6 months. Pancreatic cancer is difficult to diagnose in its early stages; at the time of diagnosis, 52% of patients have distant metastases and 26% present regional spread. Cystic lesions of the pancreas, a harbinger of pancreatic cancer, remain one of the most challenging lesions to diagnose and treat. Such cysts are frequently incidentally detected in patients undergoing abdominal imaging [i.e., computed tomography (CT) or magnetic resonance imaging (MRI)] for other indications. The most commonly occurring pancreatic cysts lack malignant potential, including retention (simple) cysts, pseudocysts and serous cystadenomas (FIG. 1). Less common are mucinous cystic neoplasms (MCNs) and intraductal papillary mucinous neoplasms (IPMNs) that have malignant potential and require surgical intervention. Some lesions, such as serous cystadenomas or pseudocysts, can be monitored, while others, such as cystic pancreatic adenocarcinomas and neuroendocrine tumors, must be promptly resected. Still more complex is the treatment of MCN, which, depending on a variety of characteristics, may or may not need to be resected.

Figure 2A:
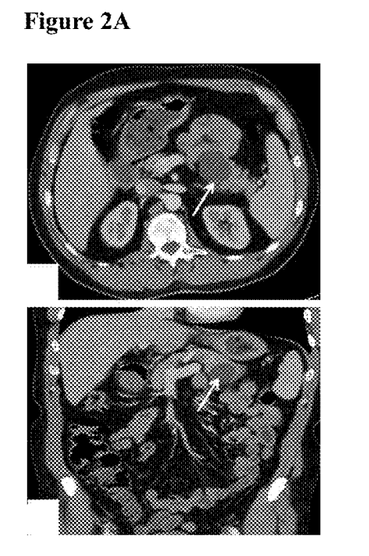
FIGS. 2A-2C. Images of pancreatic body cysts as detected by CT (FIG. 2A), MRI (FIG. 2B), EUS (FIG. 2C, upper) and EUS-FNA (FIG. 2C, lower). Arrows indicate the location of the pancreatic cyst.
Figure 2B:
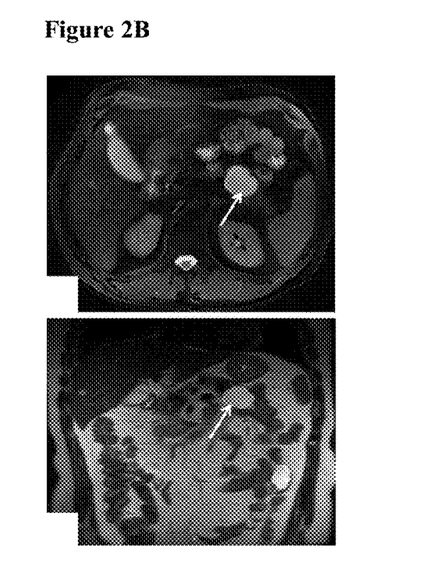
Figure 2C:
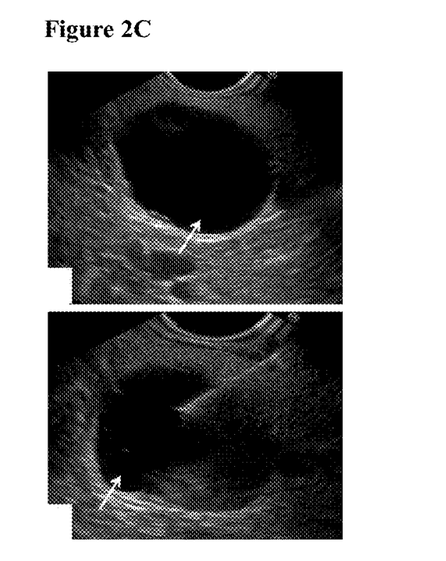

Imaging plays a vital role in both detection and characterization of pancreatic cyst lesions. An example of representative CT (FIG. 2A), MRI (FIG. 2B), and endoscopic ultrasound (EUS) (FIG. 2C) images of pancreatic body cysts, are presented in FIGS. 2A-2C. CT, MRI, and EUS can provide a clear indication of cyst location and morphology, but still suffer from inadequate diagnostic accuracy. The endoscopic ultrasound-guided fine needle aspiration method (EUS-FNA) allows for aspiration of pancreatic cyst fluid (PCF) from suspected lesions, which, upon analysis, can enhance diagnostic sensitivity and can be a helpful tool in distinguishing between benign and malignant pancreatic lesions.

PCF analysis for cytology and markers has been widely used for the differential diagnosis of pancreatic cysts (Al-Haddad et al., 2014, Gastrointestinal Endoscopy, 79: 79-87; Suzuki et al., 2014, Pancreatology, 14: 380-384; Dimaio et al., 2016, Gastrointestinal Endoscopy, 83: 1205-09; Nagashio et al., 2014, Pancreatology, 14: 503-509; Snozek et al., 2009, Clinical Biochemistry, 42: 1585-88). Among them, the carcinoembryonic antigen (CEA) marker demonstrates the highest diagnostic accuracy in discriminating between mucinous cyst (MC) and non-mucinous cyst (NMC), and in a large multicenter study, demonstrated 77% specificity and 61% sensitivity at a cutoff value of 192 ng/mL cyst fluid CEA. However, CEA levels cannot accurately differentiate between pancreatic cyst types, and therefore is not used as a stand-alone diagnostic measure. Cyst fluid amylase is a useful marker, as it is elevated in pseudocysts and cysts, such as IPMNs, that communicate with the pancreatic duct.

The rheological characteristics of the PCF can serve as an indirect measure of the concentration and structural properties of cyst fluid mucin, glycoproteins and DNA content. A common method for the characterization of PCF is the 'string-sign' method, which measures PCF properties under rapid extension. The method involves placing a sample of the aspirated fluid between the thumb and index finger and quickly separating them to measure the distance between the fingers before the sample breaks. It was reported that a higher break length of the cyst fluid correlates with a lower likelihood of a benign cyst, while a 1 mm increase in break length corresponds to a 116% increase in the likelihood of a mucinous cyst (Leung et al., 2009, Annals of Surgical Oncology, 16: 2818-24). This feature may be the result of loss of elasticity in the fluid, or disentanglement of the protein network as a result of the capillary pressure in the thread, which tends towards very high values. However, the method lacks a theoretical framework for predicting the viscoelastic nature of the cyst fluid, which can typically be characterized by the viscous and elastic response of a fluid under deformation. The viscous component relates to energy dissipated during flow, while the elastic component relates to energy stored during flow, both of which can be altered by variations in the PCF structure or composition. As an example, it was demonstrated that introduction of a small amount of protein (e.g., 0.01% w/w) into a Newtonian medium can lead to a drastic change of its viscous response, transforming to yield behavior, which is typical for structured liquids. Also, increasing the concentration of mucins in gallbladder bile fluid resulted in increased viscosity. An additional form of analysis performed on cyst fluids involves measurement of the relative viscosity of the aspirate under shear flow through a capillary. The relative viscosity of fluid from benign cysts has been shown to be significantly lower than of fluids derived from mucinous and malignant cysts. The relative viscosity of cyst fluids demonstrated high values (>1.63) in 89% of mucinous tumors and low values in all tested fluids from pseudocysts and serous cystadenomas. Relative viscosity values below the 1.63 cut-off accurately predicted non-mucinous cysts and strongly suggested that the cyst was benign (Lewandrowski et al., 1993, Annals of Surgery, 217: 41-47). In a more recent study, it was shown that relative viscosity was significantly higher for MCNs compared to pseudocysts and serous cystic tumors (1.8-1.9 and 1.2-1.3, respectively) (Linder et al., 2006, Gastrointestinal Endoscopy, 64: 697-702). Thus, the viscosity of the cyst fluids appears to be strongly affected by the nature and relative ratios of the dissolved constituents, which differ between cyst types.

Owing to the possibility of malignancy, its immediate impact on patient survival and oftentimes urgency of active intervention, there is a need to differentiate between benign and malignant pancreatic lesions. At the same time, unnecessary pancreatic operations bring with them a high mortality rate, which can be avoided by accurate diagnosis. A non-invasive method for accurate diagnosis is greatly needed.

SUMMARY OF THE INVENTION

The present invention provides methods, for determining malignancy in a cyst by measuring viscosity of cyst fluid while under stain. The invention further provides devices, and computer program products for those devices, for determining same.

According to a first aspect, there is provided a method for determining malignancy or malignant potential of a cyst, comprising,
 a. providing fluid from the cyst, and
 b. measuring viscosity of the fluid under a strain rate of at least 1000 seconds$^{-1}$,
  wherein a viscosity of at least 1.3 centipoise (cP) characterizes the cyst as malignant or potentially malignant, thereby determining malignancy or malignant potential in a cyst.

According to another aspect, there is provided a device for determining malignancy in a cyst, comprising,
 a. a chamber,
 b. a control unit, and
 c. a display,
  wherein the control unit is configured to apply a predetermined strain rate of at least 1000 seconds$^{-1}$ to fluid in the chamber and to measure the fluid's viscosity under the strain, and wherein the display provides a result of the measuring.

According to another aspect, there is provided a computer program product comprising a non-transitory computer-readable storage medium having program code embodied thereon, the program code executable by at least one hardware processor to:
 (a) measure viscosity of a fluid under a strain rate of at least 1000 seconds$^{-1}$;
 (b) compare the viscosity of the fluid to a threshold viscosity of 1.3 cP; and
 (c) provide an output regarding the malignancy of a cyst that produced the fluid.

According to some embodiments, the strain rate is at least 2000 seconds-1.

According to some embodiments, the cyst is within a subject and the providing comprises fine needle aspiration. According to some embodiments, the fine needle aspiration is endoscopic ultrasound-guided fine needle aspiration. According to some embodiments, the subject is a human.

According to some embodiments, the cyst is a pancreatic cyst.

According to some embodiments, the method further comprises analyzing at least one other factor in combination with cyst fluid viscosity, wherein the at least one other factor is selected from:
 a. age of a subject comprising the cyst;
 b. amylase levels in the cyst fluid; and
 c. carcinoembryonic antigen (CEA) levels in the cyst fluid.

According to some embodiments, the measuring viscosity is performed using a rotational viscometer. According to some embodiments, the rotational viscometer uses cone-plate geometry.

According to some embodiments, the determining malignancy or malignant potential comprises determining if the cyst is a mucinous cyst (MC) or a non-mucinous cyst (NMC). According to some embodiments, the determining comprises at least 80% accuracy.

According to some embodiments, the determining comprises greater accuracy than determining by any one of:
 a. string-sign test;
 b. measuring amylase in the fluid; and
 c. measuring CEA in the fluid.

According to some embodiments, the cyst is in a subject and further comprising removing the cyst from the subject if the viscosity is at least 1.3 centipoise (cP).

According to some embodiments, the result is a characterization of malignancy of the cyst.

According to some embodiments, characterization of malignancy of the cyst comprises comparing the viscosity under strain to a threshold viscosity of 1.3 cP and wherein a viscosity under strain of at least the threshold indicates the cyst is malignant.

According to some embodiments, the program code is further executable by at least one hardware processor to apply a strain rate of at least 1000 seconds-1 to the fluid.

According to some embodiments, a viscosity of the fluid that is at least the threshold viscosity indicates the cyst that produced the fluid is malignant.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 3A-3B.
FIGS. 4A-4B.

DETAILED DESCRIPTION OF THE INVENTION

The present invention provides, in some embodiments, methods devices and computer program products for determining malignancy in a cyst.

By one aspect, the present invention provides a method for determining rheological behavior of a cyst, the method comprises measuring viscosity of fluid from the cyst under a strain rate of at least 1000 seconds$^{-1}$, thereby determining rheological behavior of a cyst. In some embodiments, a viscosity of above 1.3 centipoise (cP) characterizes the cyst as malignant. In some embodiments, a viscosity of above 1.3 centipoise (cP) characterizes the cyst as malignant or potentially malignant. In some embodiments, a viscosity of at least 1.3 centipoise (cP) characterizes the cyst as malignant. In some embodiments, a viscosity of at least 1.3 centipoise (cP) characterizes the cyst as malignant or potentially malignant.

By another aspect, the present invention provides a method for determining malignancy in a cyst, the method comprising measuring viscosity of fluid from the cyst under a strain rate of at least 1000 seconds$^{-1}$, wherein a viscosity above 1.3 centipoise (cP) characterizes the cyst as malignant, thereby determining malignancy in a cyst.

By another aspect, the present invention provides a method for determining malignant potential in a cyst, comprising measuring viscosity of fluid from the cyst under a strain rate of at least 1000 seconds$^{-1}$, wherein a viscosity at least 1.3 centipoise (cP) characterizes the cyst as potentially malignant, thereby determining malignant potential in a cyst.

By another aspect, there is provided a method of diagnosing a subject with a cyst, the method comprising measuring viscosity of fluid from the cyst under a strain rate of at least 1000 seconds$^{-1}$, wherein a viscosity at least 1.3 centipoise (cP) determines the cyst is malignant or potentially malignant, thereby diagnosing the subject with the cyst.

By another aspect, there is provided a method of diagnosing and treating a subject with a cyst, the method comprising measuring viscosity of fluid from the cyst under a strain rate of at least 1000 seconds$^{-1}$, and if the viscosity is at least 1.3 cP removing the cyst from the subject. In some embodiments, removing the cyst comprises resecting the cyst. In some embodiments, removing the cyst comprises surgically removing the cyst.

In some embodiments, the method comprises providing fluid from a cyst. In some embodiments, the method comprises applying a strain rate of at least 1000 seconds' to the fluid. In some embodiments, method comprises measuring viscosity of the fluid under the strain rate. In some embodiments, the method comprises comparing the measured viscosity to a threshold viscosity, wherein a measured viscosity of at least the threshold viscosity determines the cyst is malignant and/or potentially malignant. In some embodiments, a viscosity of the fluid that is at least the threshold viscosity indicates the cyst that produced the fluid is malignant. In some embodiments, the threshold is 1.15, 1.2, 1.25 or 1.3 cP. In some embodiments, the threshold is 1.3 cP.

As used herein, the term "malignancy" refers to a cyst either currently containing cancerous cells or being of a high likelihood to develop cancer cells. In some embodiments, a malignant cyst is a cyst that must be resected. In some embodiments, a malignant cyst is a cyst that requires surgical intervention. In some embodiments, a malignant cyst is a cyst that must be surgically removed. In some embodiments, a malignant cyst is a mucinous cystic neoplasms (MCNs) or an intraductal papillary mucinous neoplasms (IPMNs). In some embodiments, a malignant cyst is a mucinous cyst. In some embodiments, a malignant cyst is a cancerous cyst.

In some embodiments, malignancy comprises malignant potential. As used herein, the term "malignant potential" refers to the probability that a cyst will become malignant.

In some embodiments, a potentially malignant cyst is a cyst that must be resected. In some embodiments, a potentially malignant cyst is a cyst there requires surgical intervention. In some embodiments, a potentially malignant cyst is a cyst that must be surgically removed. In some embodiments, a potentially malignant cyst is a potentially cancerous cyst.

In some embodiments, determining malignancy and/or diagnosis a subject with a cyst comprises determining if the cyst is mucinous or non-mucinous. In some embodiments, the determining and/or diagnosing comprises at least 60%, 62%, 65%, 70%, 75% or 80% accuracy. Each possibility represents a separate embodiment of the invention. In some embodiments, the determining and/or diagnosing comprises at least 80% accuracy. In some embodiments, the determining and/or diagnosing comprises at least 75% accuracy. In some embodiments, the determining and/or diagnosing comprises at least 50%, 52%, 55%, 60%, 65% or 70% sensitivity. Each possibility represents a separate embodiment of the invention. In some embodiments, the determining and/or diagnosing comprises at least 65% sensitivity. In some embodiments, the determining and/or diagnosing comprises at least 70% sensitivity. In some embodiments, the determining and/or diagnosing comprises at least 70%, 75%, 80%, 85% or 90% specificity. Each possibility represents a separate embodiment of the invention. In some embodiments, the determining and/or diagnosing comprises at least 85% specificity. In some embodiments, the determining and/or diagnosing comprises at least 90% specificity.

In some embodiments, the determining is superior to determining by any one of: string-sign test, measuring amylase in the fluid; and measuring CEA in the fluid. In some embodiments, the determining comprises greater accuracy than determining by any one of: string-sign test, measuring amylase in the fluid; and measuring CEA in the fluid. In some embodiments, the determining is superior to determining by string-sign test. In some embodiments, the determining is superior to determining by measuring amylase in the fluid. In some embodiments, the determining is superior to determining by measuring CEA in the fluid. In some embodiments, the superiority comprises any one of greater accuracy, greater specificity, and greater sensitivity. In some embodiments, the superiority comprises greater accuracy. In some embodiments, the superiority comprises greater specificity. In some embodiments, the superiority comprises greater sensitivity. In some embodiments, it is greater by at least 5, 10, 15, 20, 25, 30, 35, 40, 45 or 50%. Each possibility represents a separate embodiment of the invention.

In some embodiments, the strain rate is at least 500, 750, 1000, 1250, 1500, 1750, 2000, 2250, 2500, 2750, or 3000 seconds$^{-1}$. Each possibility represents a separate embodiment of the invention. In some embodiments, the strain rate is between 1000-3000, 1000-2750, 1000-2500, 1000-2250, 1000-2000, 1250-3000, 1250-2750, 1250-2500, 1250-2250, 1250-2000, 1500-3000, 1500-2750, 1500-2500, 1500-2250, 1500-2000, 1750-3000, 1750-2750, 1750-2500, 1750-2250, 1750-2000, 1800-2200, 1800-2000, 1900-2100, 1900-2000, 1950-2050, 1950-2000, 1975-2025, 1980-2020, 1985-2015, 1990-2010, or 1995-2005 seconds$^{-1}$. Each possibility represents a separate embodiment of the invention. In some embodiments, the strain rate is about 2000 seconds$^{-1}$. In some embodiments, the strain rate is at least 2000 seconds$^{-1}$.

In some embodiments, the cyst is within a subject. In some embodiments, the cyst is ex-vivo. In some embodiments, the subject in a human. As used herein, a "cyst" may be any type of fluid-containing or fluid-secreting abnormal growth. Examples of cyst include, but are not limited to pancreatic cysts, breast cysts, synovial cysts, dermoid cysts, and ovarian cysts. In some embodiments, the cyst is a pancreatic cyst. In some embodiments, the cyst is visible by ultrasound, CT scan or Mitt As used herein, "cyst fluid" refers to any fluid aspirated or extracted from the cyst microenvironment. In some embodiments, the cyst fluid is from within the cyst. In some embodiments, the cyst fluid is from extracellular matrix of the cyst. In some embodiments, the cyst fluid is from directly adjacent to the cyst. In some embodiments, the cyst fluid is aspirated or extracted from not more than 1 cm, 0.5 cm, 0.4 cm, 0.3 cm, 0.2 cm, 1 mm, 0.9 mm, 0.8 mm, 0.7 mm, 0.6 mm, 0.5 mm, 0.4 mm, 0.3 mm, 0.2 mm, or 0.1 mm way from the cyst. Each possibility represents a separate embodiment of the invention. In some embodiments, the cyst fluid is extracted from within the cyst.

In some embodiments, the providing comprises extracting the cyst fluid. In some embodiments, the providing comprises fine needle aspiration. In some embodiments, the fine needle aspiration is endoscopic ultrasound-guided fine needle aspiration. In some embodiments, extracting the cyst fluid comprises endoscopic ultrasound-guided fine needle aspiration. In some embodiments, extracting the cyst fluid is non-invasive.

In some embodiments, the cyst fluid is measured immediately after extraction. In some embodiments, the cyst fluid is stored at 4 degrees Celsius prior to measuring. In some embodiments, the cyst fluid is warmed to room temperature prior to measuring. In some embodiments, the cyst fluid is warmed for 30 minutes, 45 minutes, 60 minutes, 75 minutes or 90 minutes before measuring. Each possibility represents a separate embodiment of the invention. In some embodiments, the measuring is performed at 25° C.

In some embodiments, the viscosity is measured in a rheometer. In some embodiments, the viscosity is measure in a viscometer. In some embodiments, the viscometer is a rotational viscometer. In some embodiments, the rheometer and/or rotational viscometer uses cone-and-plate geometry. In some embodiments, the measuring viscosity is performed using a rheometer. In some embodiments, the measuring viscosity is performed using a viscometer. In some embodiments, the measuring viscosity is performed using a rotational viscometer.

In some embodiments, the cone diameter is about 40 mm. In some embodiments, the cone diameter is between 20-60, 20-55, 20-50, 20-45, 20-40, 25-60, 25-55, 25-50, 25-45, 25-40, 30-60, 30-55, 30-50, 30-45, 30-40, 35-60, 35-55, 35-40, 40-60, 40-55, 40-50, or 40-45 mm. Each possibility represents a separate embodiment of the invention. In some embodiments, the surface-plate angle is about 1 degree. In some embodiments, the surface-plate angle is between 0.1-2, 0.1-1.8, 0.1-1.6, 0.1-1.4, 0.1-1.2, 0.1-1.1, 0.1-1, 0.3-2, 0.3-1.8, 0.3-1.6, 0.3-1.4, 0.3-1.2, 0.3-1.1, 0.3-1, 0.5-2, 0.5-1.8, 0.5-1.6, 0.5-1.4, 0.5-1.2, 0.5-1.1, 0.5-1, 0.7-2, 0.7-1.8, 0.7-1.6, 0.7-1.4, 0.7-1.2, 0.7-1.1, 0.7-1, 0.9-2, 0.9-1.8, 0.9-1.6, 0.9-1.4, 0.9-1.2, 0.9-1.1, or 0.9-1 mm. Each possibility represents a separate embodiment of the invention. In some embodiments, viscosity is measured in shear rate control mode.

In some embodiments, the methods of the invention further comprise analyzing age of the subject in combination with cyst fluid viscosity. In some embodiments, the older the patient the greater the likelihood of malignancy. In some embodiments, the older the patient the greater the likelihood of malignant potential. In some embodiments, a subject age above 50, 55, 60, 65, 70 or 75 years increases the likelihood of malignancy or malignant potential. In some embodiments, a viscosity below 1.3 cP in combination with an advanced age characterizes a cyst as malignant or potentially malignant. In some embodiments, a viscosity no more than 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or 0.2 cP below 1.3 cP in combination with an advanced age characterizes a cyst as malignant or potentially malignant. In some embodiments, combination of subject age with a viscosity of at least 1.3 cP increases the accuracy, sensitivity and/or specificity of the method.

In some embodiments, the method of the invention further comprises analyzing at least one other factor in combination with cyst fluid viscosity, wherein the at least one other factor is selected from:

a. age of a subject comprising the cyst;
b. amylase levels in the cyst fluid; and
c. carcinoembryonic antigen (CEA) levels in the cyst fluid.

In some embodiments, higher amylase and/or CEA levels correspond to an increased risk of malignancy. In some embodiments, an amylase level of at least 60000, 70000, 80000, 90000, 100000, or 110000 U/L indicates an increased risk of malignancy. Each possibility represents a separate embodiment of the invention. In some embodiments, a CEA level of at least 1000, 1100, 1200, 1300, 1400, 1500, 1600, 1700, or 1800 ng/mL indicates an increased risk of malignancy. Each possibility represents a separate embodiment of the invention. Methods of measuring CEA and amylase in cyst fluid are well known in the art and include but are not limited to ELISA and western blot. Any method of measurement may be employed for the methods of the invention.

Devices

By another aspect there is provided a device for determining malignancy in a cyst, comprising, a chamber, and a control unit, wherein the control unit is configured to apply a predetermined strain rate of at least 1000 seconds$^{-1}$ to fluid in the chamber and to measure the fluid's viscosity under the strain. In some embodiments, the device further comprises a display. In some embodiments, the display provides a result of said measuring In some embodiments, the strain rate is at least 500, 750, 1000, 1250, 1500, 1750, 2000, 2250, 2500, 2750, or 3000 seconds$^{-1}$. Each possibility represents a separate embodiment of the invention. In some embodiments, the strain rate is between 1000-3000, 1250-2750, 1500-2500, 1750-2250, 1800-2200, 1900-2100, 1950-2050, 1975-2025, 1980-2020, 1985-2015, 1990-2010, or 1995-2005 seconds$^{-1}$. Each possibility represents a separate embodiment of the invention. In some embodiments, the strain rate is about 2000 seconds$^{-1}$.

In some embodiments, the result provided is the viscosity of the fluid. In some embodiments, the control unit compares the viscosity of the fluid to the threshold value of 1.3 cP, and when the viscosity is at least 1.3 the result is characterizing the cyst as malignant or potentially malignant. In some embodiments, the control unit compares the viscosity of the fluid to the threshold value of 1.3 cP, and when the viscosity is below 1.3 the result is characterizing the cyst as non-malignant or without malignant potential.

The terms "chip", "microchip", or "microfluidic chip" as used herein mean that the device has microfluidic form, typically but not exclusively, containing a multitude of microchannels and chambers that may or may not be interconnected with each another.

In some embodiments, the device is a biochip.

The term "biochip" is used to define a chip that is used for detection of biochemically relevant parameters from a liquid or gaseous sample. The microfluidic system of the biochip may regulate the motion of the liquids or gases on the biochip and generally may provide flow control with the aim of interaction with the analytical components, such as biosensors, for analysis of the required parameter.

The chip may include a multitude of active or passive components such as, for example and without limitation, microchannels, microvalves, micropumps, biosensors, ports, flow conduits, filters, fluidic interconnections, electrical interconnects. The terms "channel" and "microchannel" are used hereinthroughout and may comprise or be adjacent to microelectrodes, and/or related control systems.

In some embodiments, the device, in any embodiments thereof, is for use for determining or detecting one or more characteristics of a sample. In some embodiments, the sample is a biological sample. In some embodiments, the device, in any embodiments thereof, is for use in determining the malignancy of a cyst. In some embodiments, the device, in any embodiments thereof, is for use in determining the malignant potential of a cyst.

The reaction sites which are formed in the device may be of any suitable shape or form. Typically, but not exclusively, the reaction site is in the form of chambers or channels or parts thereof in fluid communication with the reagent reservoir systems. Optionally, valves may be provided between the reaction sites and the reagent reservoir systems and these may operate to control flow of sample into the reaction site from the inlet.

In some embodiments, a thermal regulation is used in the device. The term "thermal regulation" as used herein refers to the ability to control the temperature of the device. Depending on the nature of the assay carried out in the disclosed device it may be advantageous or necessary to maintain a particular temperature above ambient temperature in a component of the device, or to vary the temperature of a particular component of the device during performance of an assay. The device may therefore further include heating means for supplying heat and/or controlling the temperature in a component of the device, for example, the reaction sites, mixing units, areas of the reagent reservoir system, etc. The heating means may be integrated with the other components of the device. Suitable heating means include, for example, and without being limited thereto, electronic heater.

Optionally, the disclosed device further comprises a computer program product. In some embodiments, the computer program product compares the measured viscosity to the threshold value of 1.3 cP to characterize a cyst as malignant or potential malignant or not. Optionally, the computer program product comprises a computer-readable storage medium. The computer-readable storage medium may have program code embodied therewith.

Computer Program Product

By another aspect there is provided, a computer program product comprising a non-transitory computer-readable storage medium having program code embodied thereon, the program code executable by at least one hardware processor to: apply a strain rate of at least 1000 seconds$^{-1}$ to a fluid and measure the viscosity of the fluid under said strain rate.

In some embodiments, the program code is further executable by at least one hardware processor to: compare the viscosity of the fluid to a threshold viscosity of 1.3 cP and determine if the fluid is characteristic of a malignant cyst. In some embodiments, the program code is further executable by at least one hardware processor to provide an output regarding the malignancy of a cyst that produced the fluid. In some embodiments, a viscosity of the fluid that is at least the threshold viscosity indicates the cyst that produced the fluid is malignant.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

EXAMPLES

Materials and Methods
Study Design and Patients

The cohort consisted of 22 (11 males and 11 females) patients with a suspicious pancreatic cystic lesion, detected by cross-sectional imaging (CT and/or Mill scan) and consequentially referred for an EUS-FNA. Pancreatic cyst fluid samples were collected for cytological and biochemical analysis and patients were followed-up. In addition to routine cyst fluid analysis (biochemical, cytological and string-sign viscosity assessment), rheological measurements were performed (see below).

Pancreatic cysts were classified as mucinous (mucinous cystadenoma, mucinous adenocarcinoma, IPMN) or non-mucinous (serous cystadenoma, pseudocyst), based on surgical and/or clinical findings (presentation, follow-up, imaging and fluid analysis).

Cyst Fluid Collection and Evaluation

A curvilinear array echoendoscope (Pentax Inc. EG-3630U, Montvale, N.J.) was used to insert a 22-gauge needle (Cook Medical Inc. Bloomington, Ind., Boston expect or Olympus Inc.), under ultrasound guidance, to aspirate the cyst fluid. Cyst fluid characteristics were recorded. The levels of biochemical markers of cyst fluid CEA and amylase were measured using a commercial solid-phase double-antibody (Abbott Laboratories, Ill).

Specimens were cytopathologically analyzed for the presence of mucinous epithelium, extent of cytologic atypia and presence of malignant cells. A cellblock was prepared for further immunohistological staining.

The string-sign was determined at aspiration, by the endosonographer, as described previously (Leung et al., 2009, Annals of Surgical Oncology, 16: 2818-24), herein incorporated by reference. In brief, a drop of fluid was placed between the thumb and index finger and the maximum length of stretch before disruption of the mucous string, was measured and recorded.

Rheological Measurements

PCF samples were stored at 4° C., incubated at room temperature for one hour prior to measurements, and vortexed for 30 seconds just before testing, to ensure homogenization.

Use of a rotational viscometer supports simulation of true rheological conditions (the stepping change of either the shear stress or the shear rate is programmed but the parameter remains constant during each step). The viscosity of the PCF samples was measured with a DHR-2 Rheometer (TA Instruments, USA) at 25° C. The preferred geometry was cone-and-plate, with a cone diameter of 40 mm and a surface-plate angle of 1°. The rheometer was operated in shear rate control mode. Several time sweep tests at different constant shear rates (5-2000 1/s) were performed. The measured steady-state shear viscosity values (when the viscosity was constant in time) were used to construct flow curves of the fluids. Measurements were repeated 1-4 times for each sample, depending on the amount of fluid aspirated. The flow curves (viscosity versus shear stress or shear rate), characterizing the viscous response of the fluid under the shear field over a wide range of conditions, were then graphed.

Data Analysis

Statistical analysis was performed using the nonparametric Mann-Whitney U-test, Pearson's chi-squared test and receiver operating characteristic (ROC) curve. Cutoff points of age, CEA and viscosity were evaluated by ROC curve analysis and Youden's statistics. Sensitivity, specificity and accuracy were calculated. A p value <0.05 was considered significant. All analyses were performed using SPSS 21.0 (IBM Corp., Armonk, N.Y., USA).

Example 1

Patient Cysts Assessment

A total of 22 patients (mean age: 57.1 years [SD=16.2], Table 1) underwent endoscopic ultrasound-guided fine needle aspiration (EUS-FNA); cyst fluids were sent for cytological, biochemical and rheological assessments. Cysts were classified as MC (mucinous cystadenoma, mucinous adenocarcinoma, IPMN) or NMC (serous cystadenoma, pseudocyst), based on surgical and/or clinical findings (presentation, follow-up, imaging and fluid analyses). The baseline patient characteristics, the diameter of the cyst, the location of the cyst in the pancreas, the level of tumor markers (CEA, amylase), results of the cytological examination, string sign and rheological measurements are presented in Table 2. Overall, 10 lesions (45.45%) were classified as MC, while 12 (54.54%) were classified as NMC, 5 of which (22.72%) were considered pseudocysts.

TABLE 1

Patient age and various features of PCF samples

|  |  | Number | Mean ± SD | Median (range) | P value |
|---|---|---|---|---|---|
| Age |  | 22 (total) | 57.1 ± 16.2 | 57 (21-78) |  |
|  | MC | 10 | 69.4 ± 9.4 | 72.5 (53-78) | 0.001 |
|  | NMC | 12 | 46.8 ± 13.4 | 52.5 (21-59) |  |
|  | NMC (except PC) | 7 | 42.7 ± 15.4 | 47 (21-59) | 0.192 |
|  | PC | 5 | 52.6 ± 7.9 | 55 (39-58) |  |
| Amylase (U/L) |  | 22 (total) | 72216 ± 165518 | 1694 (22-737000) |  |
|  | MC | 10 | 89265 ± 230506 | 1694 (29-737000) | 0.692 |
|  | NMC | 12 | 58007 ± 91351 | 2149 (22-282240) |  |
|  | NMC (except PC) | 7 | 9753 ± 25457 | 68 (22-67483) | 0.012 |
|  | PC | 5 | 125563 ± 110442 | 107580 (3833-282240) |  |
| CEA (ng/mL) |  | 22 (total) | 6656 ± 22429 | 26 (0-103970) |  |
|  | MC | 10 | 14448 ± 32403 | 1305 (1-103970) | 0.034 |
|  | NMC | 12 | 162 ± 383 | 15 (0-1282) |  |
|  | NMC (except PC) | 7 | 85 ± 198 | 0 (0-531) | 0.160 |
|  | PC | 5 | 271 ± 565 | 22 (5-1282) |  |
| Cyst Diameter (mm) |  | 22 (total) | 41 ± 18 | 35 (20-80) |  |
|  | MC | 10 | 42 ± 22 | 33 (20-80) | 0.895 |
|  | NMC | 12 | 39 ± 14 | 35 (22-70) |  |
|  | NMC (except PC) | 7 | 33.29 ± 8.67 | 33 (22-50) | 0.164 |
|  | PC | 5 | 47.20 ± 17.94 | 45 (26-70) |  |
| Viscosity, $\eta_c{}^a$ |  | 22 (total) | 1.32 ± 0.33 | 1.19 (0.97-2.08) |  |
|  | MC | 10 | 1.54 ± 0.37 | 1.53 (0.99-2.08) | 0.012 |
|  | NMC | 12 | 1.14 ± 0.14 | 1.15 (0.97-1.47) |  |
|  | NMC (except PC) | 7 | 1.12 ± 0.17 | 1.05 (0.97-1.47) | 0.088 |
|  | PC | 5 | 1.17 ± 0.07 | 1.17 (1.06-1.24) |  |

$^a$Viscosity measured at strain rate $\dot\gamma$ = 2000 1/s.

TABLE 2

Patient demographics and cyst characteristics

| Sample # | Sex | Age (y) | Cyst diameter (mm) | Location | CEA (ng/mL) | Amylase (U/L) | Cytology |
|---|---|---|---|---|---|---|---|
| 1 | F | 46 | 28 | Tail | 531 | 22 | − |
| 2 | M | 47 | 22 | Body | 49.8 | 61 | − |
| 3 | F | 75 | 25 | Body | 9776 | 29 | + |
| 4 | F | 68 | 22 | Body | 286.4 | 2896 | − |
| 5 | F | 53 | 70 | Head | 24808 | 67 | + |
| 6 | F | 52 | 50 | Head | 0.1 | 67483 | − |
| 7 | F | 21 | 35 | Body | 0.1 | 64 | − |
| 8 | M | 21 | 30 | Head | 0.1 | 68 | − |
| 9 | F | 59 | 33 | Body | 0.1 | 111 | − |
| 10 | M | 77 | 35 | Head | 2324 | 7060 | − |
| 11 | F | 39 | 35 | Body | 22.2 | 107580 | − |
| 12 | M | 53 | 26 | Body | 5.1 | 282240 | − |
| 13 | M | 62 | 20 | Body | 32.8 | 27018 | + |
| 14 | F | 58 | 45 | Body | 29 | 50162 | − |
| 15 | M | 77 | 30 | Body | 2.4 | 118000 | − |
| 16 | M | 53 | 35 | Body | 12.4 | 465 | − |
| 17 | F | 70 | 70 | Tail | 1.2 | 60 | − |

TABLE 2-continued

Patient demographics and cyst characteristics

| | | | | | | | |
|---|---|---|---|---|---|---|---|
| 18 | M | 55 | 70 | Tail | 1282 | 3833 | − |
| 19 | M | 58 | 60 | Body | 18 | 184000 | − |
| 20 | M | 56 | 40 | Body | 3271 | 491 | − |
| 21 | F | 78 | 80 | Tail | 103970 | 33 | + |
| 22 | M | 78 | 30 | Body | 7.6 | 737000 | − |

| Sample # | String sign | Flow curve type | Final diagnosis | Cyst type |
|---|---|---|---|---|
| 1 | 0 | I | SC | NMC |
| 2 | 0 | III | Simple | NMC |
| 3 | 1 | II | IPMN | MC |
| 4 | 0 | I | IPMN | MC |
| 5 | 1 | III | Cancer | MC |
| 6 | 0 | I | SC | NMC |
| 7 | 1 | II | SC | NMC |
| 8 | 1 | II | SC | NMC |
| 9 | 1 | II | SC | NMC |
| 10 | 1 | III | IPMN | MC |
| 11 | 0 | II | PC | PC |
| 12 | 0 | II | PC | PC |
| 13 | 1 | II | IPMN | MC |
| 14 | 0 | II | PC | PC |
| 15 | 0 | III | IPMN | MC |
| 16 | 0 | II | SC | NMC |
| 17 | 0 | III | Cancer | MC |
| 18 | 0 | II | PC | PC |
| 19 | 1 | II | PC | PC |
| 20 | 0 | III | Cancer | MC |
| 21 | 0 | III | Cancer | MC |
| 22 | 1 | III | IPMN | MC |

Example 2

Rheological Assessment

For the rheological assessment, the extracted fluids were evaluated by both string-sign test and viscosity measurements. Flow curves were drawn up, with the viscosity, $\eta$, plotted against the shear rate, $\dot{\gamma}$. In order to describe PCF behavior across the range of shear rates, a power law model was employed:

$$\eta = \eta_\infty + K \dot{\gamma}^n \quad (1)$$

where, K and n are the fitting parameters and $\eta_\infty$ is treated as infinite viscosity.

Figure 3A:
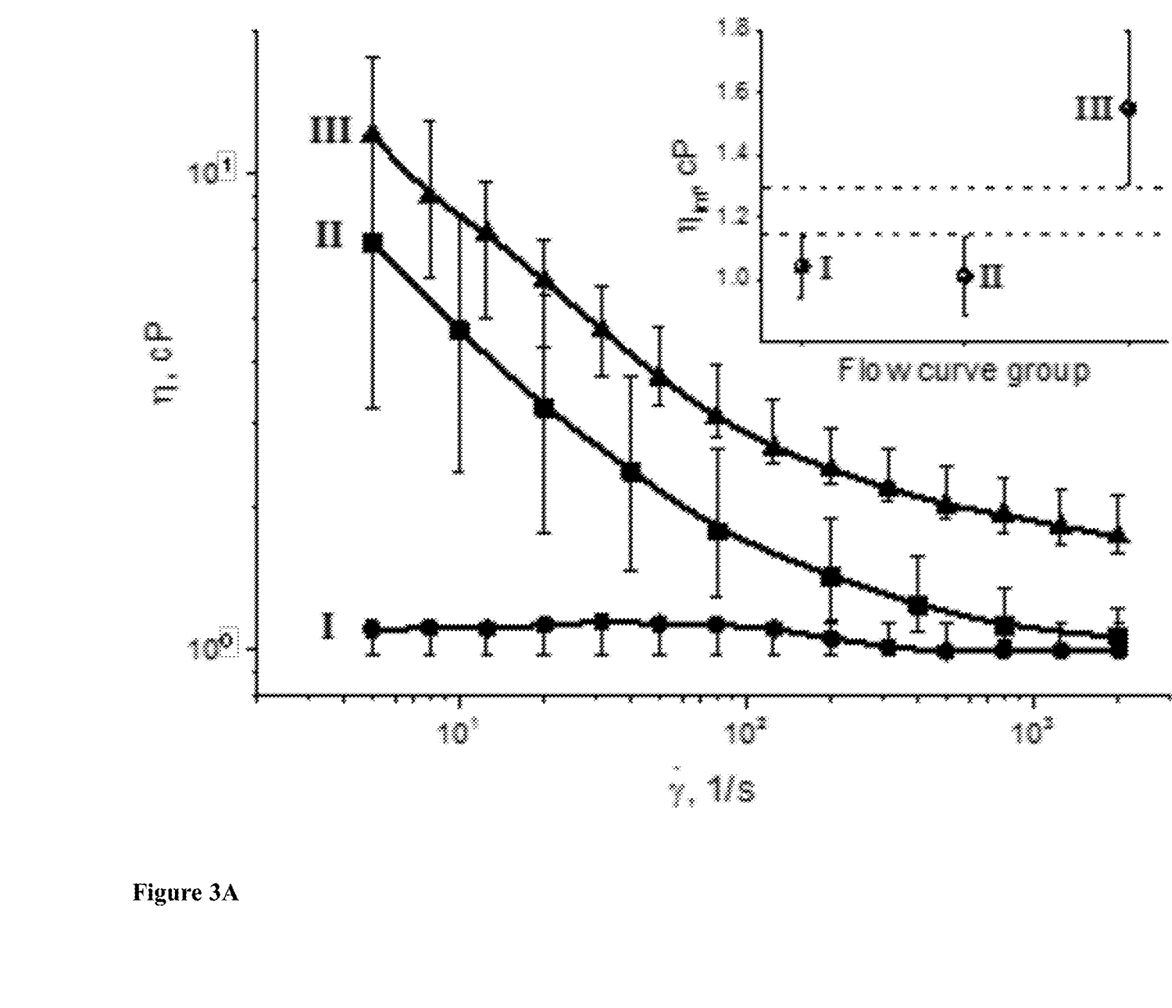
(FIG. 3A) Representative types of I, II and III flow curves. The graph inset shows the values of infinite viscosity, $\eta_\infty$, depicting the difference between the minimal value of type III and the maximum value of types I and II.
Figure 3B:
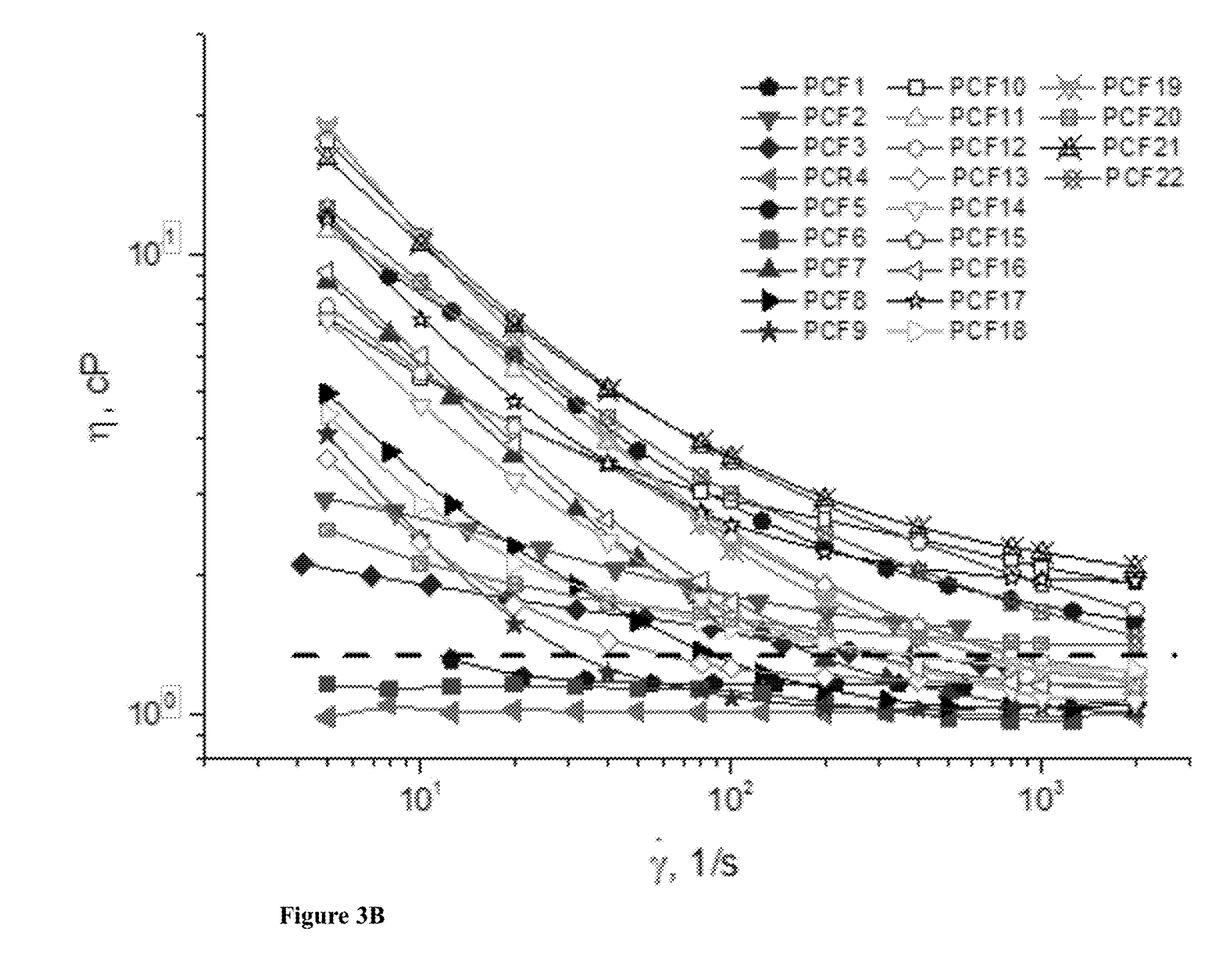
(FIG. 3B) Flow curves of the PCFs (22 samples) at 25° C.

This power law, also known as the Ostwald-de Waele power law, is typically used to describe the behavior of non-Newtonian fluids. For example, if n<1, the power law predicts that the apparent viscosity will decrease indefinitely with increasing shear rate. Fitting of the flow curves of the PCFs using Eq.1 and clustering the fitting parameters (K, n and $\eta_\infty$) (Table 3), resulted in three types of flow curves (I, II, III) (FIG. 3A). More detailed information, including flow curves, as well as the values of K, n and $\eta_\infty$ for each of the tested PCF samples, is provided herein (FIG. 3B and Table 4, respectively). At infinite shear rate, $\dot{\gamma}_\infty$, type II and I flow curves demonstrated nearly similar low viscosity, $\eta_\infty=1.01$ cP and $\eta_\infty=1.04$ cP respectively, while a significantly higher infinite viscosity, $\eta_\infty=1.55$ cP, was found for type III. In addition, at low shear rates, the viscosity of type III samples was one order of magnitude higher than the type I samples, and double that of the type II samples, indicating an entirely different fluid micro-structure. Based on the diagnostic results determined using clinical findings (Table 1), we can induce that NMCs display types I or II rheological behavior, while MCs display type III flow curves. Statistical analysis of the flow curve classifications (Table 3) demonstrated a significant difference in the rheological behavior of MCs (flow curve III) versus NMCs (flow curves I and II) (p<0.0001). It is evident in the inset of FIG. 3A, that confidence intervals for flow curves of type III and that of the types I and II do not overlap, and that the difference between the minimal value of infinite viscosity of group III and the maximum value of $\eta_\infty$ of types I and II, marked by dash lines, covers the range of $\eta_\infty=1.15$-$1.30$ cP. These findings indicate that $\eta_\infty$ is a potentially suitable marker for distinguishing between MC and NMC. However, infinite viscosity is an extrapolated value, thus, it was decided to measure the viscosity, $\eta_c$, at high shear rates (i.e., $\dot{\gamma}=2000$ 1/s); they proved similar to those determined at $\dot{\gamma}_\infty$.

TABLE 3

Averaged values of the model parameters for the PCF samples

| Flow curve type # | (cP) $\eta_\infty$ | K | n |
|---|---|---|---|
| I | 1.04 ± 0.10 | <10⁻⁵ | ≈0 |
| II | 1.01 ± 0.13 | 0.025 ± 0.018 | −0.79 ± 0.25 |
| III | 1.55 ± 0.26 | 0.026 ± 0.019 | −0.62 ± 0.17 |

TABLE 4

Fitting parameters of the power law model for all tested PCFs

| Flow curve type # | PCF sample # | , cP $\eta_\infty$ | K | n |
|---|---|---|---|---|
| I | 1 | 1.16 | 1.52 × 10⁻⁹ | −0.002797 |
| | 4 | 0.99 | 9.9 × 10⁻⁶ | −0.000409 |
| | 6 | 0.97 | 9.9 × 10⁻⁶ | −0.000409 |
| II | 3 | 0.85 | 0.0019 | −0.177 |
| | 7 | 0.91 | 0.0278 | −0.775 |

TABLE 4-continued

Fitting parameters of the power law model for all tested PCFs

| Flow curve type # | PCF sample # | $\eta_\infty$, cP | K | n |
|---|---|---|---|---|
| | 8 | 0.92 | 0.0143 | −0.785 |
| | 9 | 0.99 | 0.0203 | −1.175 |
| | 11 | 1.00 | 0.0394 | −0.712 |
| | 12 | 0.80 | 0.0149 | −0.484 |
| | 13 | 1.14 | 0.0127 | −1.028 |

TABLE 4-continued

Fitting parameters of the power law model for all tested PCFs

| Flow curve type # | PCF sample # | $\eta_\infty$, cP | K | n |
|---|---|---|---|---|
| | 14 | 0.98 | 0.0203 | −0.736 |
| | 16 | 1.05 | 0.0288 | −0.781 |
| | 18 | 1.19 | 0.0129 | −0.858 |
| | 19 | 1.04 | 0.0716 | −0.863 |
| | 22 | 1.22 | 0.0305 | −0.612 |
| III | 2 | 1.34 | 0.0033 | −0.412 |
| | 5 | 1.41 | 0.0355 | −0.693 |
| | 10 | 1.57 | 0.0105 | −0.435 |
| | 15 | 1.33 | 0.0431 | −0.638 |
| | 17 | 1.88 | 0.0423 | −0.896 |
| | 20 | 1.36 | 0.0026 | −0.521 |
| | 21 | 1.94 | 0.0456 | −0.727 |

Example 3

Diagnostic Capacity of Tested Factors

For the purpose of comparing between predictive factors in their diagnostic capacity to differentiate between mucinous and non-mucinous PCFs, the statistical significance of mean values measured for flow curve types I and II versus III are presented in Table 5. It can be seen that CEA levels were significantly lower among NMCs as compared to MCs ($p<0.014$). No significant difference in amylase levels was observed between MC versus NMC, although the levels were increased significantly in pseudocysts, as compared to other NMCs (Table 2). It is important to mention that patients with MCs were older than those with NMCs (69.4 and 46.8 years old, respectively). Moreover, there was no substantial difference in cyst diameters between MC and NMC lesions. However, mean viscosity $\eta_c$ values were significantly different between type I and II lesions versus type III lesions ($p<0.0001$).

TABLE 5

Mean values of predictive factors in PCF sample subgroups

| | Flow curve | Number | Mean ± SD | Median (range) | P value |
|---|---|---|---|---|---|
| Age (60 y) | | 22 (total) | 57.1 ± 16.2 | 57 (21-78) | |
| | I | 3 | 55.3 ± 11.4 | 52 (46-68) | |
| | II | 11 | 50.4 ± 16.8 | 55 (21-75) | |
| | I + II | 14 | 51.4 ± 15.5 | 54 (21-75) | 0.020 |
| | III | 8 | 7 ± 12.9 | 73.5 (47-78) | |
| Amylase (U/L) | | 22 (total) | 72216 ± 165518 | 1694 (22-737000) | |
| | I | 3 | 23467 ± 38146 | 2896 (22-67483) | |
| | II | 11 | 59597 ± 94488 | 3833 (29-282240) | |
| | I + II | 14 | 51855 ± 85605 | 3365 (22-282240) | 0.297 |
| | III | 8 | 107847 ± 257487 | 279 (33-737000) | |
| CEA (ng/mL) | | 22 (total) | 6656 ± 22429 | 26 (0-103970) | |
| | I | 3 | 273 ± 266 | 286 (0-531) | |
| | II | 11 | 1016 ± 2930 | 18 (0-9776) | |
| | I + II | 14 | 857 ± 2591 | 20 (0-9776) | 0.014 |
| | III | 8 | 16804 ± 36218 | 1187 (1-103970) | |
| Cyst Diameter (mm) | | 22 (total) | 40.5 ± 18.1 | 35 (20-80) | |
| | I | 3 | 33.33 ± 14.74 | 28 (22-50) | |
| | II | 11 | 37.64 ± 15.19 | 35 (20-70) | |
| | I + II | 14 | 36.71 ± 14.64 | 34 (20-70) | 0.294 |
| | III | 8 | 47.13 ± 22.5 | 37.5 (22-80) | |
| Viscosity, $\eta_c$ (cP) | | 22 (total) | 1.32 ± 0.33 | 1.19 (0.97-2.08) | |
| | I | 3 | 1.04 ± 0.1 | 0.99 (0.97-1.15) | |
| | II | 11 | 1.13 ± 0.08 | 1.15 (1.01-1.24) | |
| | I + II | 14 | 1.11 ± 0.09 | 1.15 (0.97-1.24) | <0.0001 |
| | III | 8 | 1.69 ± 0.26 | 1.64 (1.41-2.08) | |

$\eta_c$ - Viscosity measured at strain rate $\dot{\gamma}$ = 2000 1/s.

Example 4

Cyst Fluid Viscosity as a Predictive Factor

Figure 4A:
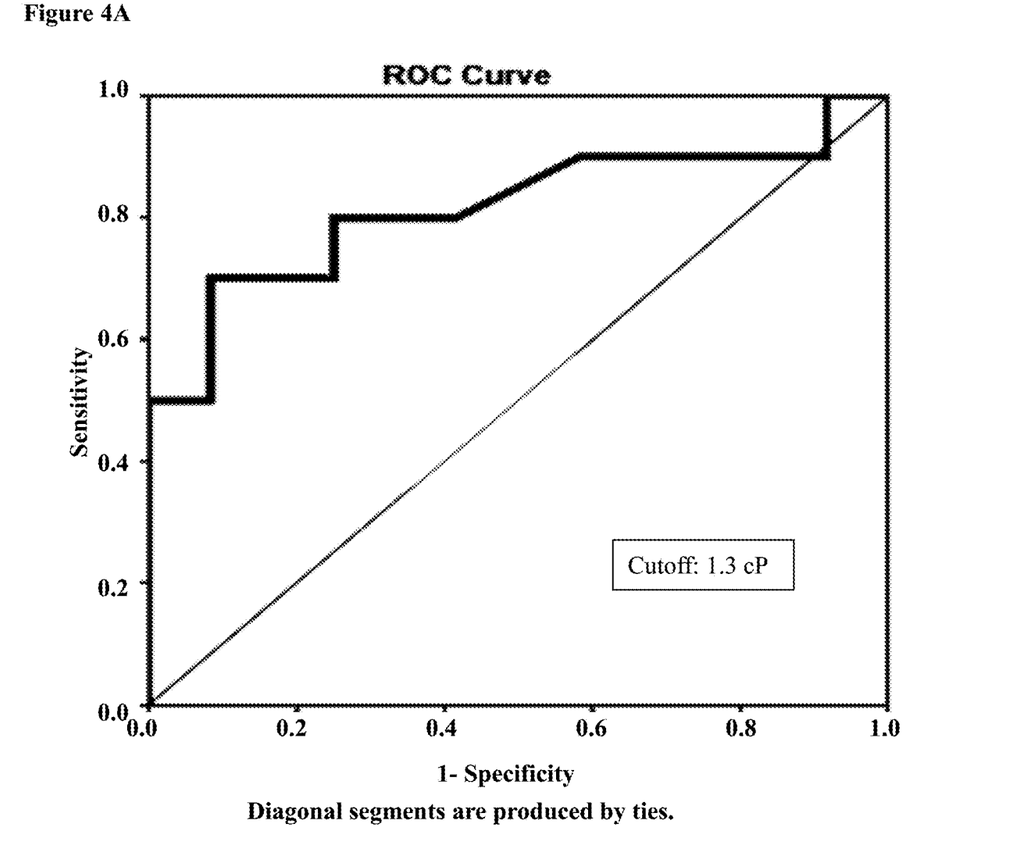
(FIG. 4A) Receiver operator characteristic (ROC) curve evaluating the performance of cyst fluid viscosity, $\eta_c$, measured at strain rate $\dot{\gamma}$=2000 1/s.
Figure 4B:
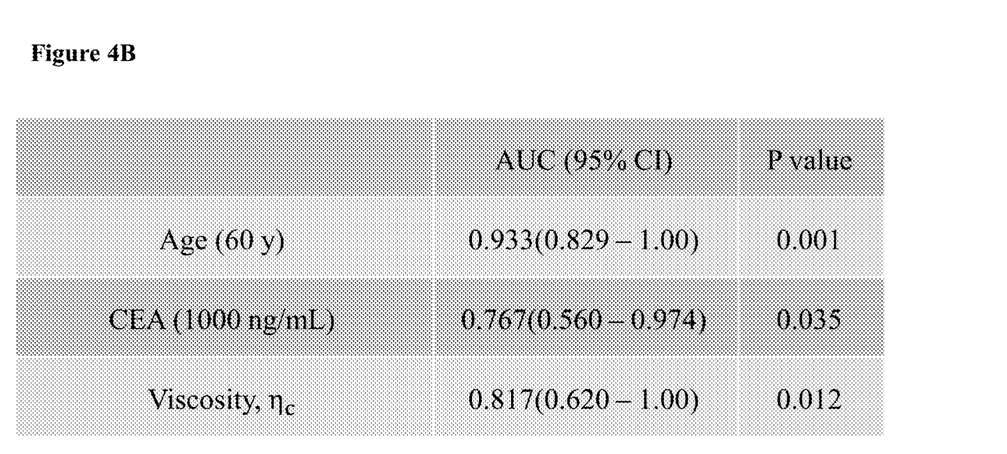
(FIG. 4B) ROC analysis of age, CEA and $\eta_c$ in differentiation between MCN vs. NMC.

Receiver operator curve analysis of the cyst fluid viscosity, $\eta_c$, established that the optimal cutoff value for differentiating between MC (flow curve III) versus NMC (flow curve I and II) cysts was 1.3 cP (FIG. 4A), with area under the curve (AUC) of 0.817 (FIG. 4B). The sensitivity, specificity and accuracy of cystic fluid CEA, amylase, cytology, string sign, age, viscosity $\eta_c$ and various combinations of these criteria used to predict whether the cysts were MC or NMC, are presented in Table 6. Using the optimal cutoff value, the sensitivity, specificity, and accuracy of cyst fluid viscosity $\eta_c$-based diagnosis of MC versus NMC were 70%, 91.7%, and 81.8%, respectively. In comparison, string-sign analysis showed a sensitivity, specificity and accuracy of only 50%, 66.7%, and 59.1%, respectively. The overall accuracy of the viscosity-based technique (81.8%) was greater than that of CEA (72.7%), amylase (50%), cytology (72.7%) and string-sign (59.1%). When considering cyst fluid viscosity, $\eta_c$ jointly with patient age, the sensitivity and the accuracy increased to 100% and 95.5%, respectively, but the specificity remained 91.7%.

TABLE 6

Statistical parameters of various diagnostic approaches
for differentiating between MC versus NMC lesions

| Method | Sensitivity | Specificity | PPV | NPV | Accuracy | P value |
|---|---|---|---|---|---|---|
| Age | 0.800 | 1.00 | 1.00 | 0.857 | 0.909 | 0.000 |
| String-Sign | 0.500 | 0.667 | 0.556 | 0.615 | 0.591 | 0.666 |
| CEA (192 ng/mL) | 0.600 | 0.833 | 0.750 | 0.714 | 0.727 | 0.074 |
| CEA (1000 ng/mL) | 0.500 | 0.917 | 0.833 | 0.688 | 0.727 | 0.056 |
| Amylase (1200 U/L) | 0.500 | 0.500 | 0.455 | 0.545 | 0.500 | 1.000 |
| PC/NMC- Amylase (1200 U/L) | 1.00 | 0.857 | 1.00 | 0.857 | 0.917 | 0.015 |
| Cytology | 0.400 | 1.00 | 1.00 | 0.667 | 0.727 | 0.029 |
| Viscosity, $\eta_c$ | 0.700 | 0.917 | 0.875 | 0.786 | 0.818 | 0.006 |
| Combinations | | | | | | |
| CEA (192 ng/mL) + Amylase (1200 U/L) | 0.200 | 0.917 | 0.667 | 0.579 | 0.591 | 0.571 |
| CEA (192 ng/mL) + Amylase (1200 U/L) + string sign | 0.600 | 0.833 | 0.750 | 0.714 | 0.727 | 0.074 |
| string sign + CEA (192 ng/mL) | 0.700 | 0.583 | 0.583 | 0.700 | 0.636 | 0.231 |
| Viscosity, $\eta_c$ + CEA (192 ng/mL) | 0.900 | 0.750 | 0.900 | 0.900 | 0.818 | 0.004 |
| Viscosity, $\eta_c$ + Age (I + II & <60) | 1.00 | 0.917 | 1.00 | 1.00 | 0.955 | 0.000 |
| Viscosity, $\eta_c$ + CEA (1000 ng/mL) | 0.800 | 0.833 | 0.800 | 0.833 | 0.818 | 0.008 |

PPV positive predictive value, NPV negative predictive value $\eta_c$ - Viscosity measured at strain rate $\dot{\gamma}$ = 2000 1/s.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for determining malignancy or malignant potential of a cyst, comprising,
    a. providing fluid from said cyst, and
    b. measuring viscosity of said fluid under a strain rate of at least 1000 seconds$^{-1}$,
    wherein a viscosity of at least 1.3 centipoise (cP) characterizes said cyst as malignant or potentially malignant, thereby determining malignancy or malignant potential in a cyst.

2. The method of claim 1, wherein said strain rate is at least 2000 seconds$^{1}$.

3. The method of claim 1, wherein said cyst is within a subject and said providing comprises fine needle aspiration.

4. The method of claim 3, wherein said fine needle aspiration is endoscopic ultrasound-guided fine needle aspiration.

5. The method of claim 3, wherein said subject is a human.

6. The method of claim 1, wherein said cyst is a pancreatic cyst.

7. The method of claim 1, further comprising analyzing at least one other factor in combination with cyst fluid viscosity, wherein said at least one other factor is selected from:
    a. age of a subject comprising said cyst;
    b. amylase levels in said cyst fluid; and
    c. carcinoembryonic antigen (CEA) levels in said cyst fluid.

8. The method of claim 7, comprising analyzing cyst fluid viscosity in combination with age of a subject comprising said cyst.

9. The method of claim 1, wherein said measuring viscosity is performed using a rotational viscometer.

10. The method of claim 9, wherein said rotational viscometer uses cone-plate geometry.

11. The method of claim 1, wherein said determining malignancy or malignant potential comprises determining if said cyst is a mucinous cyst (MC) or a non-mucinous cyst (NMC).

12. The method of claim 1, wherein said determining comprises at least 80% accuracy.

13. The method of claim 1, wherein said determining comprises greater accuracy than determining by all of:
    a. string-sign test;
    b. measuring amylase in said fluid; and
    c. measuring CEA in said fluid.

14. The method of claim 1, wherein said cyst is in a subject and further comprising removing said cyst from said subject if said viscosity is at least 1.3 centipoise (cP).

15. A device for determining malignancy in a cyst, comprising,
    a. a chamber,
    b. a control unit, and
    c. a display,
    wherein said control unit is configured to apply a predetermined strain rate of at least 1000 seconds$^{-1}$ to fluid in said chamber and to measure said fluid's viscosity under said strain, and wherein said display provides a characterization of malignancy of said cyst.

16. The device of claim 15, wherein the strain rate is at least 2000 seconds$^{1}$.

17. The device of claim 15, wherein characterization of malignancy of said cyst comprises comparing said viscosity under strain to a threshold viscosity of 1.3 cP and wherein a viscosity under strain of at least said threshold indicates said cyst is malignant.

18. A computer program product comprising a non-transitory computer-readable storage medium having program code embodied thereon, the program code executable by at least one hardware processor to:
    (a) measure viscosity of a fluid under a strain rate of at least 1000 seconds$^{-1}$;
    (b) compare said viscosity of said fluid to a threshold viscosity of 1.3 cP; and
    (c) provide an output regarding the malignancy of a cyst that produced said fluid, wherein a viscosity of said fluid that is at least the threshold viscosity indicates said cyst that produced said fluid is malignant.

19. The computer program product of claim 18, wherein the program code is further executable by at least one hardware processor to apply a strain rate of at least 1000 seconds$^{-1}$ to said fluid.

* * * * *